United States Patent
Petersen et al.

(10) Patent No.: US 10,721,572 B2
(45) Date of Patent: Jul. 21, 2020

(54) HEARING AID INCLUDING A VIBRATOR TOUCHING A PINNA

(71) Applicant: Oticon A/S, Smørum (DK)

(72) Inventors: Svend Oscar Petersen, Smørum (DK); Thor Højlund Olsen, Smørum (DK); Bjarke Mejnertsen, Smørum (DK)

(73) Assignee: OTICON A/S, Smørun (DK)

( * ) Notice: Subject to any disclaimer, the term of this patent is extended or adjusted under 35 U.S.C. 154(b) by 0 days.

(21) Appl. No.: 16/262,435

(22) Filed: Jan. 30, 2019

(65) Prior Publication Data

US 2019/0239006 A1    Aug. 1, 2019

(30) Foreign Application Priority Data

Jan. 31, 2018  (EP) ..................... 18154395

(51) Int. Cl.
*H04R 25/00* (2006.01)
*A61N 1/05* (2006.01)
*G02C 11/06* (2006.01)

(52) U.S. Cl.
CPC .......... *H04R 25/606* (2013.01); *H04R 25/40* (2013.01); *H04R 25/453* (2013.01); *H04R 25/65* (2013.01); *A61N 1/0541* (2013.01); *G02C 11/06* (2013.01); *H04R 25/405* (2013.01); *H04R 25/604* (2013.01); *H04R 2225/021* (2013.01); *H04R 2225/67* (2013.01); *H04R 2460/13* (2013.01)

(58) Field of Classification Search
CPC .... H04R 1/1016; H04R 1/105; H04R 1/1058; H04R 25/658; H04R 25/652
See application file for complete search history.

(56) References Cited

U.S. PATENT DOCUMENTS

| | | | | |
|---|---|---|---|---|
| RE27,487 E | * | 9/1972 | Hassler | H04R 1/406 381/313 |
| 4,904,078 A | * | 2/1990 | Gorike | G02C 11/06 351/158 |
| 8,842,870 B2 | * | 9/2014 | East | H04R 1/1066 381/173 |
| 9,020,168 B2 | * | 4/2015 | Karkkainen | H04R 1/1075 381/151 |
| 9,720,259 B2 | * | 8/2017 | Hart | G02C 7/04 |
| 9,980,054 B2 | * | 5/2018 | McCracken | H04R 25/405 |
| 10,231,046 B1 | * | 3/2019 | Miller | H04R 1/028 |
| 10,506,343 B2 | * | 12/2019 | Hosoi | H04R 1/02 |
| 2002/0039427 A1 | * | 4/2002 | Whitwell | H04R 1/1091 381/312 |
| 2004/0208333 A1 | * | 10/2004 | Cheung | H04S 1/00 381/333 |

(Continued)

FOREIGN PATENT DOCUMENTS

EP    0 836 364 A2    4/1998
EP    0 836 364 A3    3/2003

(Continued)

*Primary Examiner* — Oyesola C Ojo
(74) *Attorney, Agent, or Firm* — Birch, Stewart, Kolasch & Birch, LLP

(57) ABSTRACT

A hearing aid is disclosed. The hearing aid comprises a carrier unit and a vibrator unit provided on said carrier unit. The vibrator unit is configured to apply vibrations to a pinna of an outer ear of a user by touching said pinna.

17 Claims, 11 Drawing Sheets

(56) References Cited

U.S. PATENT DOCUMENTS

| | | | | |
|---|---|---|---|---|
| 2005/0248717 A1* | 11/2005 | Howell | G02C 5/001 | 351/41 |
| 2007/0025574 A1* | 2/2007 | Azima | H04R 1/1075 | 381/330 |
| 2008/0260189 A1* | 10/2008 | Schobben | H04R 25/405 | 381/313 |
| 2010/0110368 A1* | 5/2010 | Chaum | G02B 27/017 | 351/158 |
| 2011/0091057 A1* | 4/2011 | Derkx | H04R 25/407 | 381/313 |
| 2013/0051585 A1* | 2/2013 | Karkkainen | H04R 1/1075 | 381/151 |
| 2013/0342806 A1* | 12/2013 | Sathe | H04R 1/46 | 351/158 |
| 2014/0268016 A1* | 9/2014 | Chow | G02C 11/10 | 351/158 |
| 2014/0348363 A1* | 11/2014 | Edwards | H04R 25/604 | 381/326 |
| 2015/0071479 A1* | 3/2015 | East | H04R 1/1066 | 381/381 |
| 2015/0131838 A1* | 5/2015 | Horii | G02C 11/10 | 381/381 |
| 2015/0156595 A1* | 6/2015 | Zhong | H04R 25/606 | 381/326 |
| 2015/0181338 A1* | 6/2015 | Hosoi | H04M 1/03 | 381/309 |
| 2015/0312686 A1* | 10/2015 | Gustafsson | H04R 25/606 | 600/25 |
| 2016/0183014 A1* | 6/2016 | Guo | G10L 25/78 | 381/23.1 |
| 2016/0275817 A1* | 9/2016 | Chen | G09B 21/006 | |
| 2017/0238096 A1* | 8/2017 | Nakagawa | H04R 1/1091 | 381/310 |
| 2018/0020299 A1 | 1/2018 | Nilsson | | |
| 2018/0078422 A1* | 3/2018 | Dierenbach | H04R 25/402 | |
| 2019/0104352 A1* | 4/2019 | Ozawa | H04R 1/24 | |
| 2019/0113774 A1* | 4/2019 | Anderson | G02C 5/143 | |
| 2019/0253809 A1* | 8/2019 | Kunimoto | H04B 1/44 | |

FOREIGN PATENT DOCUMENTS

| | | |
|---|---|---|
| EP | 2 254 345 A1 | 11/2010 |
| EP | 3 010 248 A1 | 4/2016 |
| JP | 2001-320790 A | 11/2001 |
| WO | 2014/097744 † | 6/2014 |
| WO | WO 2014/097744 A1 | 6/2014 |

\* cited by examiner
† cited by third party

HEARING AID INCLUDING A VIBRATOR TOUCHING A PINNA

TECHNICAL FIELD

The present disclosure relates to hearing aids. More particularly, the disclosure relates to measures for realizing less noticeable and comfortable to wear hearing aids.

BACKGROUND

A general problem in designing a hearing aid is to deliver enough acoustical gain for the user in a broad frequency range (usually from 100 Hz to 10.000 Hz) depending on the hearing loss. This is usually achieved by either placing a speaker in an earpiece into the ear canal or by placing a loudspeaker behind the ear and lead the sound through a tube into the ear canal.

To achieve great output in the lower frequencies, the earpiece needs to seal well to the ear canal, and the venting in the earpiece needs to be small. This usually results in physical comfort problems for the user as well as the occlusion effect, making the users own voice uncomfortable. Additionally, users also dislike having something visible going into the ear canal.

An alternative way of delivering sound to the user's ear is through bone conduction. This is used in bone-anchored hearing aids for users with conductive hearing losses. In such case, the sound output is delivered as vibration to the skull. The vibrations travel through the skull bone and into the cochlear where the user can hear it as sound.

In the bone anchored solutions, the user gets a connector operated into the skull bone behind the ear, which the bone anchored hearing aid physically connects to.

For more mild hearing conductive hearing losses, the bone conducting hearing aid can also connect to the surface of the skin, either by using a head band or adhesive tape that hold the hearing aid towards the skin.

The bone-conducting hearing aid can also be built into hearing glasses, where the bone conducting transducer is placed behind the ear on the skin against the skull bone.

All of these bone conducting hearing aid related solutions usually require some force against the skin in order to deliver enough vibration to the user. This force can be uncomfortable for the user. These bone conducting hearing aid related solutions are generally acceptable for users with primarily conductive hearing loss, but usually not efficient enough for users with sensor-neural hearing loss (age related hearing loss).

The bone conducting hearing aids solves the problems with respect to comfort in the ear canal and visibility of something going into the ear canal. A problem is usually to get enough sound output through the skin on the skull bone. Further, at high output levels, the vibrations cause tingling discomfort on the skin, where the user can feel the vibrations.

Besides, hearing glasses is a smart way of combining hearing aids with glasses and opens up for a more discreet solution for users needing both.

There are two types of hearing glasses, namely, either having bone conducting (BC) transducers or air conducting (AC) transducers (or a combination of BC and AC).

The BC versions are a smart way of making a discreet delivery of the sound for the users through vibrations through the skin and skull into the user's cochlea. However, BC versions are limited by the low maximum force output (MFO), especially through the skin in the higher frequencies.

The AC versions do not have the same problems with maximum power output (MPO). The AC versions are usually constructed by having a speaker unit attached with a wire to the temple of the glasses and the other end of the wire to the speaker placed in the ear canal, similar to a receiver-in-the-ear (RITE) style hearing aid. There are also known AC versions with a speaker build into the temple of the glasses and then having a tube that leads the sound into an earpiece in the ear canal, similar to a behind-the-ear (BTE) style hearing aid. Both AC versions, with either a wire or a tube, make the hearing glasses less discreet and reduce the usability of the glasses. Namely, the earpiece is to be replaced every time the glasses are taken on and off.

Therefore, there is a need to provide a solution that addresses at least some of the above-mentioned problems. The present disclosure provides at least an alternative to the prior art.

SUMMARY

An object of the disclosed invention is to provide a hearing aid. The hearing aid comprises a carrier unit and a vibrator unit provided on said carrier unit. The vibrator unit is configured to apply vibrations to a pinna of an outer ear of a user by touching said pinna.

In the hearing aid, the vibrator unit may be configured to touch a rear part of said pinna.

In the hearing aid, the vibrator unit may be configured to vibrate substantially perpendicular to a touching interface with said pinna.

The hearing aid may be a behind-the-ear hearing aid. In such case, the carrier unit may be a housing of said behind-the-ear hearing aid. Further, the vibrator unit may be mounted on said housing of said behind-the-ear hearing aid.

When the hearing aid is a behind-the-ear hearing aid, the hearing aid may further comprise a speaker unit, a speaker driver unit configured to drive said speaker unit, and an earpiece. The speaker unit may be electrically connected to said speaker driver unit. Further, the speaker unit may be provided in said earpiece. Alternatively, the speaker unit may be provided in said housing of said behind-the-ear hearing aid and connected to said earpiece by means of a sound tube.

When the hearing, aid is a behind-the-ear hearing aid, the hearing aid may further comprise at least one microphone unit, and a vibrator driver unit configured to drive said vibrator unit. The vibrator driver unit may be configured to, if said at least one microphone unit is activated, deactivate driving said vibrator unit.

The hearing aid may be an eyeglass hearing aid. In such case, the carrier unit may be a temple of said eyeglass hearing aid. Further, the vibrator unit may be mounted on said temple of said eyeglass hearing aid.

When the hearing aid is an eyeglass hearing aid, the hearing aid may further comprise a frame of said eyeglass hearing aid, wherein the frame includes said temple. The hearing aid may further comprise at least one microphone unit provided on said frame of said eyeglass hearing aid, a directional speaker unit configured to direct sound towards an ear canal of said user and to attenuate sound towards said at least one microphone unit, and a signal processing unit configured to output signals to said directional speaker unit.

The directional speaker unit may comprise a first speaker unit and a second speaker unit arranged such that a distance between said first speaker unit or a speaker outlet of said first speaker unit and said at least one microphone unit is substantially same as a distance between said second speaker unit or a speaker outlet of said second speaker unit and said at least one microphone unit. The first speaker unit and said second speaker unit may be connected in series and opposite in phase.

Alternatively, the directional speaker unit may comprise a first speaker unit and a second speaker unit arranged such that a distance between said first speaker unit or a speaker outlet of said first speaker unit and said at least one microphone unit is larger than a distance between said second speaker unit or a speaker outlet of said second speaker unit and said at least one microphone unit. The signal processing unit may be configured to output a first signal to said first speaker unit and to output a second signal different from said first signal to said second speaker unit.

In the latter case, the signal processing unit may be configured to apply said first signal with a delay and a gain with respect to said second signal.

Further, in the latter case, the signal processing unit may be configured to multiply said first signal with a weighting including at least one of an amplitude value and a phase value.

The weighting may be frequency band dependent.

Further, in the latter case, the signal processing unit may be configured to process signals with a predetermined sample time. Assuming that the difference between said distance between said first speaker unit or said speaker outlet of said first speaker unit and said at least one microphone unit and said distance between said second speaker unit or said speaker outlet of said second speaker unit and said at least one microphone unit is a difference distance, the difference distance equals a distance that sound propagates at a numerical multitude of said predetermined sample time.

In either case, each of said first speaker unit and said second speaker unit may be provided with a respective vibration cancellation unit configured to cancel out vibrations from said respective speaker unit towards said frame of said eyeglass hearing aid.

Further, in general, the vibrator unit may be an electrodynamic transducer, a balanced electrodynamic separation transducer, or a piezo electrical transducer.

According to a further object of the present disclosure, there is provided a hearing aid. The hearing aid comprises at least one microphone unit, and a directional speaker unit configured to direct sound towards an ear canal of a user and to attenuate sound towards said at least one microphone unit.

The hearing aid may be an eyeglass hearing aid comprising a frame. In such case, the directional speaker unit is provided on said frame.

Preferably, the frame comprises a temple, and the directional speaker unit is provided on said temple.

When the hearing aid is an eyeglass hearing aid, the at least one microphone unit may be provided on the frame of the eyeglass hearing aid.

The hearing aid may further comprise a signal processing unit configured to output signals to said directional speaker unit.

The directional speaker unit may comprise a first speaker unit and a second speaker unit arranged such that a distance between said first speaker unit or a speaker outlet of said first speaker unit and said at least one microphone unit is substantially same as a distance between said second speaker unit or a speaker outlet of said second speaker unit and said at least one microphone unit. The first speaker unit and said second speaker unit may be connected in series and opposite in phase.

Alternatively, the directional speaker unit may comprise a first speaker unit and a second speaker unit arranged such that a distance between said first speaker unit or a speaker outlet of said first speaker unit and said at least one microphone unit is larger than a distance between said second speaker unit or a speaker outlet of said second speaker unit and said at least one microphone unit. The signal processing unit may be configured to output a first signal to said first speaker unit and to output a second signal different from said first signal to said second speaker unit.

In the latter case, the signal processing unit may be configured to apply said first signal with a delay and a gain with respect to said second signal.

Further, in the latter case, the signal processing unit may be configured to multiply said first signal with a weighting including at least one of an amplitude value and a phase value.

The weighting may be frequency band dependent.

Further, in the latter case, the signal processing unit may be configured to process signals with a predetermined sample time. Assuming that the difference between said distance between said first speaker unit or said speaker outlet of said first speaker unit and said at least one microphone unit and said distance between said second speaker unit or said speaker outlet of said second speaker unit and said at least one microphone unit is a difference distance, the difference distance equals a distance that sound propagates at a numerical multitude of said predetermined sample time.

In either case, each of said first speaker unit and said second speaker unit may be provided with a respective vibration cancellation unit configured to cancel out vibrations from said respective speaker unit towards said frame of said eyeglass hearing aid.

BRIEF DESCRIPTION OF DRAWINGS

The objects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each object may each be combined with any or all features of the other objects. These and other objects, features and/or technical effect will be apparent from and elucidated with reference to the illustrations described hereinafter in which:

DETAILED DESCRIPTION

Figure 1:
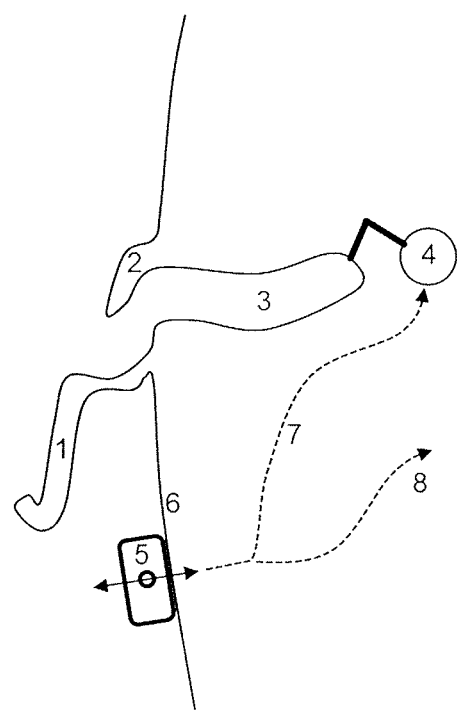
FIG. 1 illustrates a transducer arranged according to a conventional bone conducting system.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

A hearing device may include a hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. The "hearing device" may further refer to a device such as an earphone or a headset adapted to receive an audio signal electronically, possibly modifying the audio signal and providing the possibly modified audio signals as an audible signal to at least one of the user's ears. Such audible signals may be provided in the form of an acoustic signal radiated into the user's outer ear, or an acoustic signal transferred as mechanical vibrations to the user's inner ears through bone structure of the user's head and/or through parts of middle ear of the user or electric signals transferred directly or indirectly to cochlear nerve and/or to auditory cortex of the user.

The hearing device is adapted to be worn in any known way. This may include i) arranging a unit of the hearing device behind the ear with a tube leading air-borne acoustic signals into the ear canal or with a receiver/loudspeaker arranged close to or in the ear canal such as in a Behind-the-Ear type hearing aid, and/or ii) arranging the hearing device entirely or partly in the pinna and/or in the ear canal of the user such as in a In-the-Ear type hearing aid or In-the-Canal/Completely-in-Canal type hearing aid, or iii) arranging a unit of the hearing device attached to a fixture implanted into the skull bone such as in Bone Anchored Hearing Aid or Cochlear Implant, or iv) arranging a unit of the hearing device as an entirely or partly implanted unit such as in Bone Anchored Hearing Aid or Cochlear Implant.

A "hearing system" refers to a system comprising one or two hearing devices, and a "binaural hearing system" refers to a system comprising two hearing devices where the devices are adapted to cooperatively provide audible signals to both of the user's ears. The hearing system or binaural hearing system may further include auxiliary device(s) that communicates with at least one hearing device, the auxiliary device affecting the operation of the hearing devices and/or benefitting from the functioning of the hearing devices. A wired or wireless communication link between the at least one hearing device and the auxiliary device is established that allows for exchanging information (e.g. control and status signals, possibly audio signals) between the at least one hearing device and the auxiliary device. Such auxiliary devices may include at least one of remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing device. The remote control is adapted to control functionality and operation of the at least one hearing devices. The function of the remote control may be implemented in a Smartphone or other electronic device, the Smartphone/electronic device possibly running an application that controls functionality of the at least one hearing device.

In general, a hearing device includes i) an input unit such as a microphone for receiving an acoustic signal from a user's surroundings and providing a corresponding input audio signal, and/or ii) a receiving unit for electronically receiving an input audio signal. The hearing device further includes a signal processing unit for processing the input audio signal and an output unit for providing an audible signal to the user in dependence on the processed audio signal.

The input unit may include multiple input microphones, e.g. for providing direction-dependent audio signal processing. Such directional microphone system is adapted to enhance a target acoustic source among a multitude of acoustic sources in the user's environment. In one aspect, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. The signal processing unit may further be adapted to provide other relevant functionality such as compression, noise reduction, etc. The output unit may include an output transducer such as a loudspeaker/receiver for providing an air-borne acoustic signal transcutaneously or percutaneously to the skull bone or a vibrator for providing a structure-borne or liquid-borne acoustic signal. In some hearing devices, the output unit may include one or more output electrodes for providing the electric signals such as in a Cochlear Implant.

It is now referred to FIG. 1, which illustrates a transducer arranged according to a conventional bone conducting system.

In the conventional bone conducting system illustrated in FIG. 1, the bone conductor 5 (BC transducer, vibrating in the direction of the arrows) is interfacing the skin on the skull 6 usually behind the ear. In FIG. 1, an ear is schematically illustrated, including, inter alia, the pinna 1, the tragus 2, the ear canal 3, and the cochlear 4. It is difficult to get the vibrations through the skin and into the skull bone without applying a large pressure on the skin. If the pressure is too low all the vibration energy is used to vibrate the skin, and very little vibration gets into the skull bone and further into the cochlear 4. Reference sign 7 denotes vibrations from BC transducer 5 traveling via the bone 6 into the cochlear 4. A large constant pressure onto the skin achieves a better transmission of the vibrations into the skull, but the larger pressure will cause discomfort over time. Reference sign 8 denotes vibrations traveling in particular in such case through the skull bone 6 to other ear as well.

Figure 2:
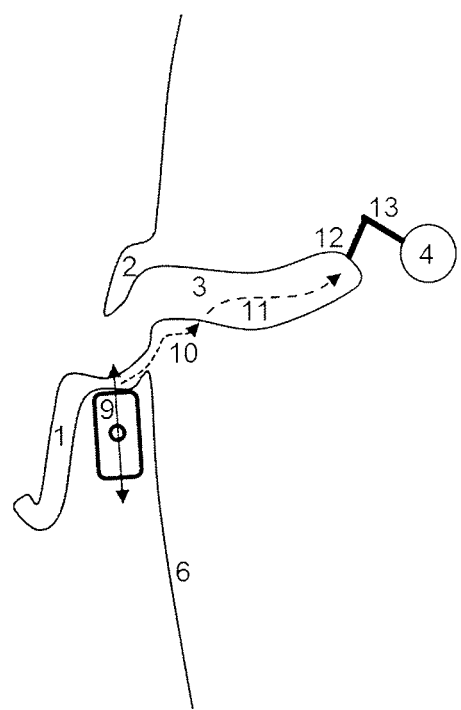
FIG. 2 illustrates a pinna touching/conducting transducer according to an embodiment of the disclosure.

It is now referred to FIG. 2, which illustrates a pinna touching/conducting transducer according to an embodiment of the disclosure.

According to the present disclosure, the bone conducting transducer 9 (vibrating in the direction of the arrows) is interfaced to the rear part 1a of the pinna 1 instead of onto the skull or the skin on the skull behind the ear. By interfacing the back of the pinna 1 the vibrations from the transducer 9 travel through the flesh and bone into the cochlear 4, but the vibration also generates a sound pressure level in the ear canal 3 especially in the low frequencies (100-2000 Hz) when the skin and tissue around the ear canal 3 vibrates. Reference sign 10 denotes vibrations from the BC transducer 9 traveling through the cartilage into the ear canal 3. Reference sign 11 denotes vibrations of the cartilage generating sound pressure in the ear canal 3 that travels to the eardrum 12, thereby stimulating malleus, incus and stapes 13 of the ear.

In other words, in general, the bone conducting transducer 9 is placed behind the pinna 1 and touching said pinna 1 (in particular the back 1a of the pinna).

More preferably, the bone conducting transducer 9 may be placed behind the pinna 1 and touching the part of the pinna 1, which is behind the concha.

The advantage of placing the bone conducting transducer 9 behind the concha compared to other places on the pinna, is that the transducer 9 is less visible and the vibrations from the transducer 9 are more effectively transferred to the eardrum 12 via the concha and the ear canal 3.

The reason for not placing a transducer 9 behind the concha is due to lack of possibilities of fasten the vibrator to the ear. For example using an adhesive material or a clamp attached to the vibrator and fasten to the outer part of the pinna, are both solutions which are either inconvenient to use or is more visible to the surrounding. In the case where the bone conducting transducer 9 is mounted on to a surface of a hearing aid, such as a Behind-the-ear (BTE) hearing aid or an eyeglass hearing aid, then the fastening is provided by the hearing aid. For example, all three components of a BTE hearing aid including, a housing configured to be placed behind the ear and a connection part configured to connect the housing with an earpiece, will together provide a stable fastening of the transducer 9 on to the concha. Another example, a frame of the eyeglass hearing aid will provide the fastening of the transducer 9 to the concha. Both examples illustrate a convenient way of wearing the transducer 9, since the user is able take it on or off. Using an adhesive material to fasten the transducer 9 will result in difficulties in removing the transducer 9, and probably, skin defects due to multiple on or off actions.

Users with conductive hearing loss may not benefit greatly from the sound generated in the ear canal 3, but users with sensor neural hearing loss would. In the present disclosure, the type of transducer 9 is named pinna conducting transducer or pinna touching transducer or pinna conductor.

As can be seen in FIG. 2 when comparing with FIG. 1 illustrating a conventional bone conducting system, by touching the pinna 1, and vibrating perpendicular to the touching interface, the cartilage of the pinna 1 is vibrating. The vibrations travels through the cartilage into the ear canal 3, where the vibrations generate sound pressure in the ear canal 3 that is picked up by the eardrum 12.

An advantage of the pinna conductor 9 of the present disclosure is that very little pressure is needed to transmit the vibrations into the cartilage, since the softness or compliance of the skin and cartilage is very similar.

A further advantage of the pinna conductor 9 of the present disclosure is that the vibrations only reaches the ear on the side of the instrument, where, as mentioned above, the conventional bone conducting system as illustrated in FIG. 1 generates vibrations to the cochlears 4 on both sides of the head. Thus, the pinna conductor 9 of the present disclosure generates a more natural sounding signal to the user, where directional information of sound can be maintained.

Figure 3:
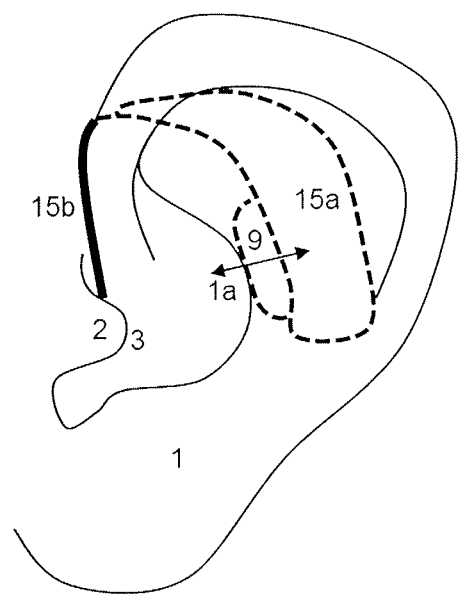
FIG. 3 illustrates a pinna touching/conducting transducer arranged with a behind-the-ear part of a hearing aid according to an embodiment of the disclosure.

It is now referred to FIG. 3, which illustrates a pinna touching/conducting transducer 9 arranged with a behind-the-ear part of a hearing aid according to an embodiment of the disclosure.

In particular, FIG. 3 illustrates a possible implementation of a pinna conducting transducer 9, wherein the pinna conducting transducer 9 (vibrating in the direction of the arrows) is built into the behind-the-ear part 15a of a hearing aid, i.e., a behind-the-ear-hearing aid. The pinna conducting transducer 9 interfaces with the rear part 1a of the pinna 1 and delivers sound in low frequencies (<1500 Hz), while sound in high frequencies (≥1500 Hz) is delivered through a RITE speaker in the ear canal (connected to the behind-the-ear part via a speaker unit wire 15b) or a speaker in the behind-the-ear part through a tube 15b in the ear canal 3.

An advantage of such implementation is that the earpiece can be fitted with an open fitting. An open fitting prevents the conventional speaker from delivering a sound in the low frequencies (<1500 Hz). However, according to the present disclosure, the pinna conductor 9 can deliver the low frequency sounds.

Figure 4:
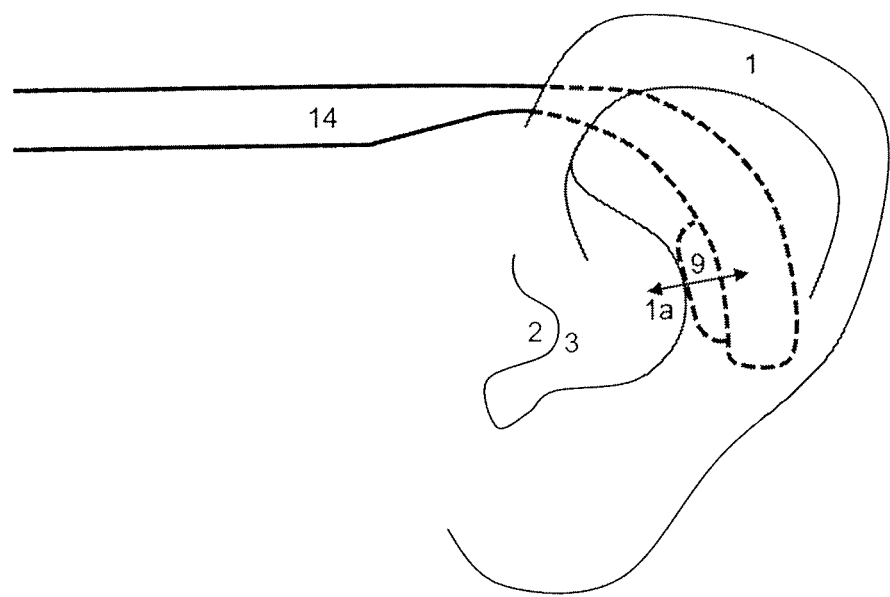
FIG. 4 illustrates a pinna touching/conducting transducer arranged with a part of an eyeglass of an eyeglass hearing aid according to an embodiment of the disclosure.

It is now referred to FIG. 4, which illustrates a pinna touching/conducting transducer arranged with a part of an eyeglass of an eyeglass hearing aid according to an embodiment of the disclosure.

In particular, FIG. 4 illustrates a further possible implementation of a pinna conducting transducer 9 in a hearing system. The system is a combination of glasses (spectacles comprising a temple 14 or corresponding part of a frame) and the hearing aid, that is, an eyeglass hearing aid. The pinna conducting transducer 9 (vibrating in the direction of the arrows) is placed in the temple tip of the glasses and interfaces with the rear part 1a of the pinna 1. Consequently, the vibration is directed to the ear canal 3 behind the tragus 2.

The system may also include one or more microphones, a sound processor, and an amplifier.

One possible approach according to the present disclosure to address potential mechanical feedback of the pinna conducting transducer 9 to microphones also arranged on the frame of the eyeglass hearing aid or on the housing of the behind-the-ear hearing aid, when used for amplifying the ambient sound is that the pinna conducting transducer 9 may be deactivated in case the microphone(s) is(are) activated, and may be activated only in a case where sound is streamed from e.g. an external device (i.e. smartphone, mp3-player, etc.).

Further, an echo canceller (not shown) may be provided in order to compensate for echo potentially occurring in the above-outlined streaming scenario.

In general, pinna conducting transducer 9 according to the present disclosure may be, for example, an electrodynamic transducer, a balanced electrodynamic separation transducer or a piezo electrical transducer.

Further, in systems in which the pinna conducting transducer 9 is utilized in combination with air conducting transducers, as for example discussed in relation to FIG. 3, the pinna conducting transducer 9 is preferably utilized for sounds of frequencies on and below 2 kHz, while the air conducting transducers (for example speakers of a directional speaker unit discussed below) are preferably utilized for sounds of frequencies above 2 kHz.

Figure 5:
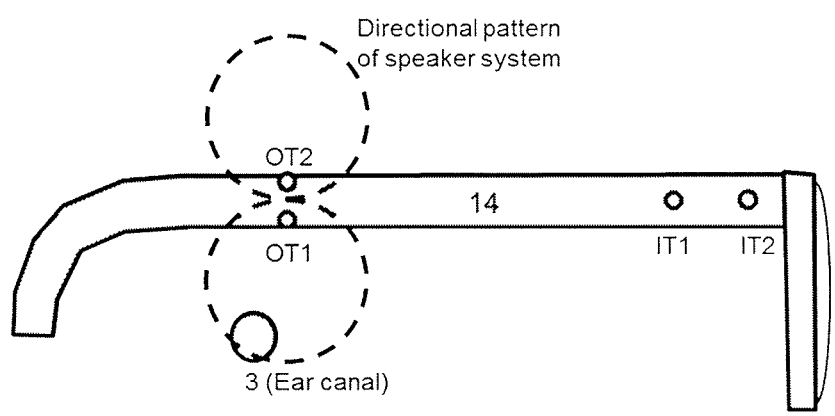
FIG. 5 illustrates an arrangement of a directional speaker unit according to an embodiment of the disclosure.

It is now referred to FIG. 5, which illustrates an arrangement of a directional speaker unit according to an embodiment of the disclosure.

Namely, in combination with the above-discussed pinna conducting transducer and also without provision thereof, according to embodiments of the present disclosure, a directional speaker (OT1, OT2) may be built into the frame (or temple 14) of the hearing glasses (eyeglass hearing aid), that directs sound towards the user's ear canal 3, and attenuates the sound in other directions especially towards microphones (IT1, IT2) also provided on the eyeglass hearing aid, preferably on the frame of the eyeglass hearing aid, and more preferably on a temple 14 thereof.

According to the present disclosure, the microphone(s) shall ideally not pick up the sound from the outputting transducers (OT1, OT2), since this would cause the hearing instrument to oscillate if the gain is too high.

Hearing glasses implementing the concept of the present disclosure look like normal glasses with no visible signs of being a hearing aid. In particular, there are no tubes or wires going into the ear canal 3.

In FIG. 5, a simple directional speaker being a dipole speaker is illustrated. As is shown in FIG. 5, the two speakers (OT1, OT2) of the dipole speaker (or the respective outlets of the two speakers) are arranged one above the other such that the distance of each of the two speakers (or the respective outlets of the two speakers) to the microphone(s) (input transducers IT1, IT2) is the same.

According to the present disclosure, the two speakers are connected in opposite phase so that when one speaker is outputting a positive sound pressure, the other speaker is outputting a negative sound pressure. As a result, a directional pattern (dipole directional output pattern) indicated by the dashed circles can be achieved.

Figure 7:
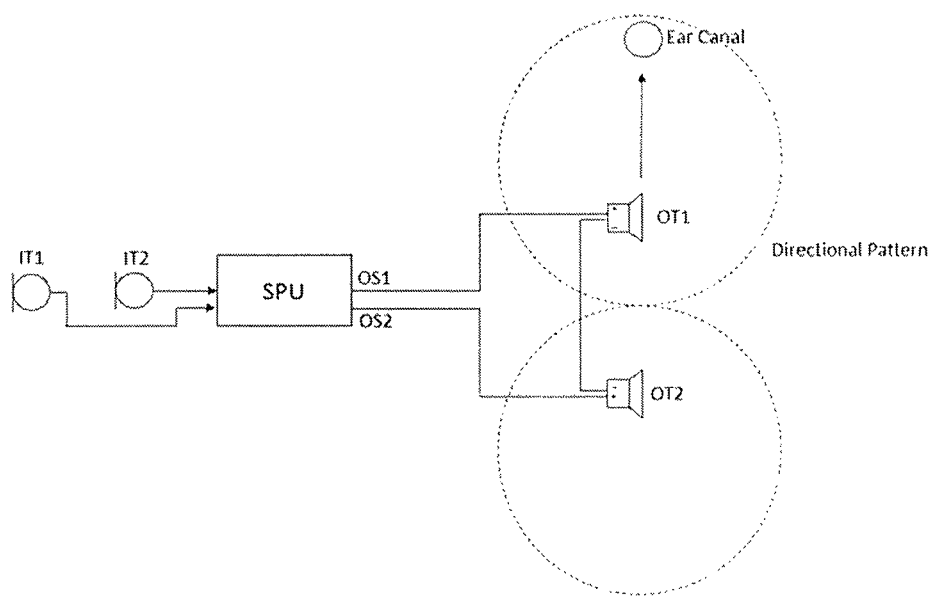
FIG. 7 illustrates a circuit layout for controlling a directional speaker unit according to an embodiment of the disclosure.

FIG. 7 illustrates a circuit layout for controlling the directional speaker unit comprising the dipole speaker illustrated in FIG. 5 according to an embodiment of the disclosure.

As can be seen in FIG. 7, input signals of the input transducers (microphones) IT1, IT2 are input to a signal processing unit SPU which converts those signals to output signals. As a result, the output signals OS1, OS2 are respectfully output to the output transducers (speakers of the dipole speaker) OT1, OT2, such that the two speakers connected in series and in opposite phase with respect to the signals input thereto generate respective sound pressure in the opposite phases, to thereby achieve the directional pattern indicated by the dashed circles.

The directional pattern is such that the sound is directed towards the user's ear canal 3, and is attenuated towards the microphones IT1, IT2. In other words, the directional pattern shows a maximum output towards the ear canal 3 and a minimum output towards the input transduces IT1, IT2.

The dipole speaker implementation according to the present disclosure requires no additional signal processing to create the directional output patterns. In other words, sound processing for determining/providing the directionality is less complicated since delay between the two speakers does not have to be included in the algorithm.

Figure 10:
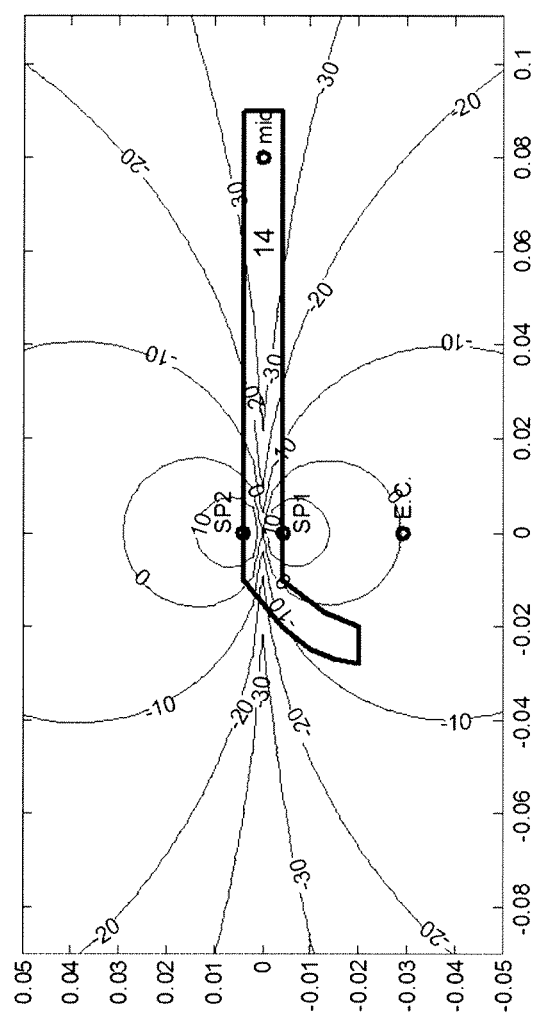
FIG. 10 illustrates a sound pressure level distribution resulting from deployment of a directional speaker unit according to an embodiment of the disclosure.

FIG. 10 illustrates a sound pressure level distribution resulting from deployment of a directional speaker unit according, to an embodiment of the disclosure.

In particular, FIG. 10 illustrates a specific example application of the directional speaker unit comprising the dipole speaker illustrated in FIG. 5 and the circuit layout for controlling the directional speaker unit illustrated in FIG. 7.

Here, the contour lines show a relative sound pressure level from the directional speaker around the temple 14 of the frame of the eyeglass hearing aid.

In the example, a height of the temple 14 is 8 mm. Accordingly, the two speakers/output transducers (SP1, SP2) of the dipole speaker (or the respective outlets of the two speakers) are placed 8 mm apart from each other and in equal distance to the input transducers (mic) 80 mm away. The ear canal 3 (E.C.) is positioned 25 mm below the output transducer SP1.

As can be seen in FIG. 10, the simulated sound pressure at the microphones is about 40 dB lower than at the ear canal (about 0 dB).

As a modification of the embodiment of the present disclosure, for a simple dipole speaker, the two speakers (OT1, OT2) may be replaced by one speaker with two outlets.

Figure 6:
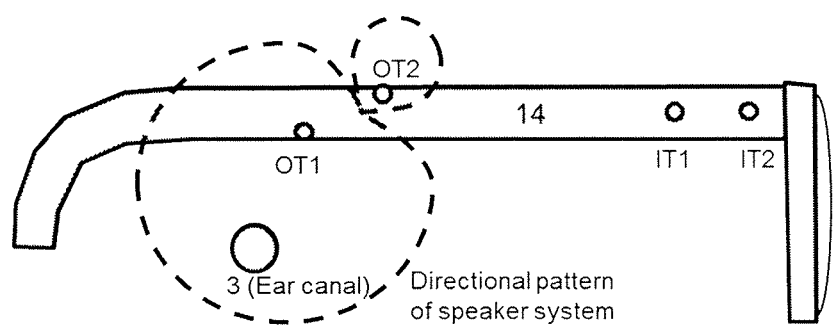
FIG. 6 illustrates an arrangement of a directional speaker unit according to an embodiment of the disclosure.

It is now referred to FIG. 6, which illustrates an alternative arrangement of a directional speaker unit according to an embodiment of the disclosure.

The configurable directional speaker shown in FIG. 6 allows to create a more directional output to thereby generate a higher output to the ear canal 3.

Namely, as is shown in FIG. 6, two speakers (OT1, OT2) of a configurable directional speaker (or the respective outlets of the two speakers) are arranged such that the distance of each of the two speakers (or the respective outlets of the two speakers) to the microphone(s) (input transducers IT1, IT2) differs from each other.

The speaker OT2 (or outlet thereof) is closer to the microphones IT1, IT2 on the temple 14 of the glasses frame. The directional output pattern of the speakers is set such that the cancellation angle is directed towards the microphone(s) IT1, IT2.

This arrangement allows creation of higher output towards the ear canal 3.

However, this arrangement requires additional signal processing in order to steer the directionality into the intended direction (based on the positional relationship between the speakers OT1, OT2, the microphones IT1, IT2, and the ear canal 3). In particular, the delay between the two speakers OT1, OT2 towards the ear canal 3 has to be included in the algorithm of the sound processing. Though, when arranging the output transceivers/speakers OT1, OT2 or the respective outlets of the two speakers horizontally offset, the frame 14 of the glasses may be designed less high.

Figure 8:
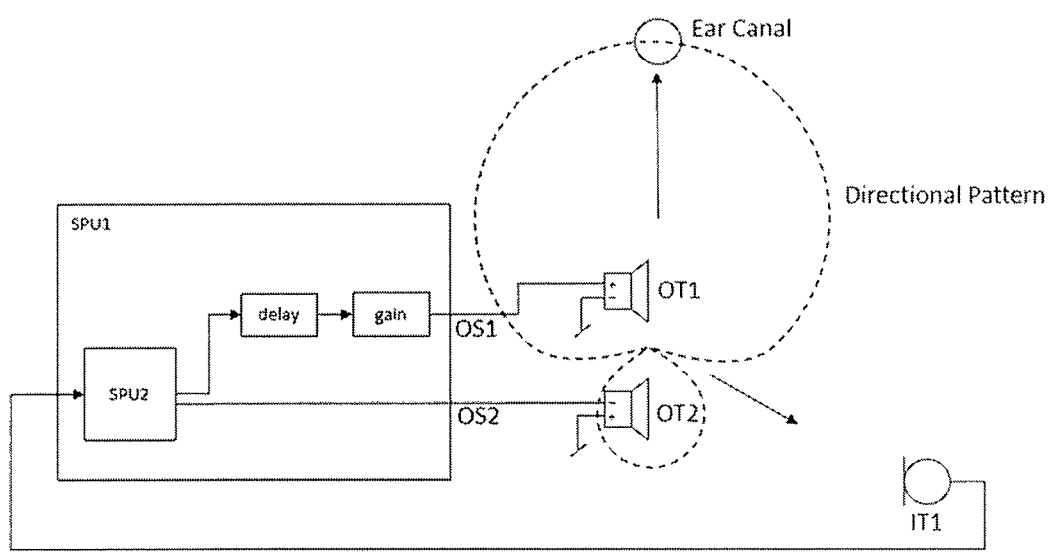
FIG. 8 illustrates a circuit layout for controlling a directional speaker unit according to an embodiment of the disclosure.

FIG. 8 illustrates a circuit layout for controlling the directional speaker unit, i.e., the configurable directional speaker illustrated in FIG. 6, according to an embodiment of the disclosure.

As can be seen in FIG. 8, an input signal of an input transducer (microphone) IT1 (or more input transducers) is input to a signal processing unit SPU1, SPU2 which converts this signal to output signals OS1, OS2. The output signal OS1 to one speaker OT1 is applied with a delay and a gain with respect to the output signal OS2 to the other speaker OT2. Accordingly, the signal processing unit SPU1 comprises a delay unit configured to apply a delay and a gain unit configured to apply a gain.

The output signals OS1, OS2 are respectfully output to the output transducers OT1, OT2, such that the two speakers generate respective sound pressure, to thereby achieve the directional pattern indicated by the dashed circles.

Namely, by adding a delay to (the signal provided to) the one speaker (output transducer) OT1 that corrects for the difference in distance from the input transducers to OT1 and OT2, and by adding a gain to (the signal provided to) the one speaker (output transducer) OT1 that corrects for a difference in sound pressure level (SPL) from OT1 and OT2 at the input transducers, the circuit layout illustrated in FIG. 8 according to an embodiment of the present disclosure allows to customize/configure the directional output pattern of the configurable directional speaker to minimize the output of the speakers of the directional speaker unit (i.e., the configurable directional speaker) towards the microphone, and on the same time to have a high output towards the ear canal 3.

As a modification, a delay and/or gain may be applied to both signals to be respectively output as output signals OS1 and OS2. Namely, to achieve the advantage of the embodiment of the present disclosure, a delay difference and a gain difference is to generated at to the outputs to the two speakers OT1, OT2 in the directional speaker system FIG. 9 illustrates an alternative circuit layout for controlling the directional speaker unit, i.e., the configurable directional speaker illustrated in FIG. 6, according to an embodiment of the disclosure.

Figure 9:
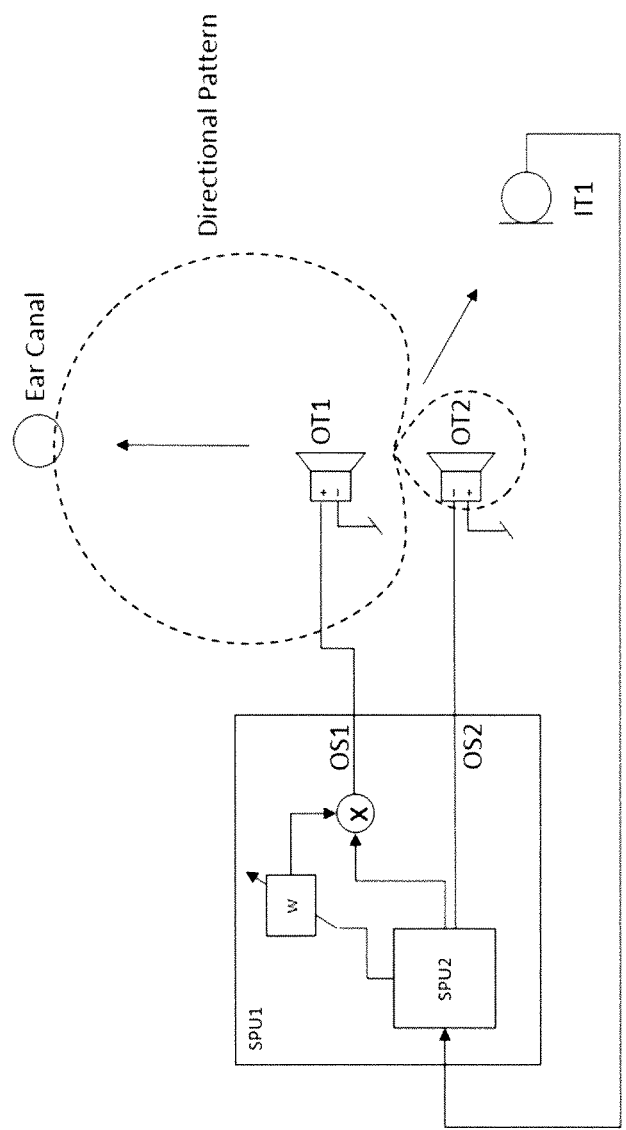
FIG. 9 illustrates a circuit layout for controlling a directional speaker unit according to an embodiment of the disclosure.

As can be seen in FIG. 9, an input signal of an input transducer (microphone) IT1 (or more input transducers) is input to a signal processing unit SPU1, SPU2 which converts this signal to output signals OS1, OS2. The output signal OS1 to one speaker OT1 is applied with a weighting with respect to the output signal OS2 to the other speaker OT2. Accordingly, the signal processing unit SPU1 comprises a weighting unit configured to set a weighting and a multiplication unit configured to multiply the signal to be output as output signal OS1 with the weighting.

The output signals OS1, OS2 are respectfully output to the output transducers (speakers of the dipole speaker) OT1, OT2, such that the two speakers generate respective sound pressure, to thereby achieve the directional pattern indicated by the dashed circles.

According to this embodiment of the present disclosure, the configurable directional speaker may be adaptive in that the weighting is made adaptive. In particular, the sound processing unit SDU2 may adaptively find/set the weightings so as to minimize feedback at/towards the input transducers.

According to the present disclosure, the weighting, may be multiplied to the output signals in the frequency domain.

Further, the weightings may be controlled in separate (sub) frequency bands in a frequency domain implementation, i.e., with a weighting, for each frequency band.

Further, the weightings may include an amplitude value and/or a phase value.

Figure 11:
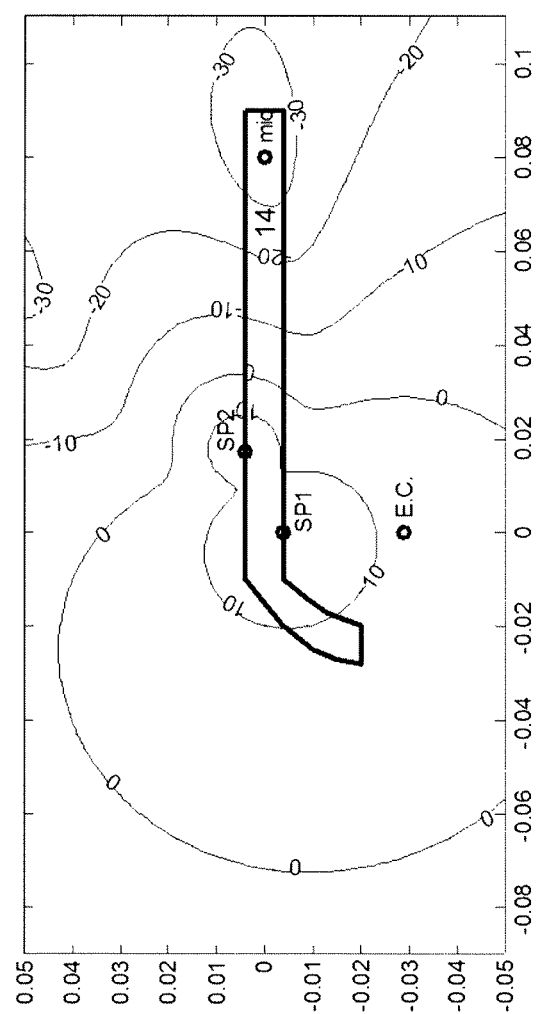
FIG. 11 illustrates a sound pressure level distribution resulting from deployment of a directional speaker unit according to an embodiment of the disclosure.

FIG. 11 illustrates a sound pressure level distribution resulting from deployment of a directional speaker unit according to an embodiment of the disclosure.

In particular, FIG. 11 illustrates a specific example application of the directional speaker unit, i.e., the configurable directional speaker illustrated in FIG. 6 and the circuit layout for controlling the directional speaker unit illustrated in FIG. 8.

Here, the contour lines show a relative sound pressure level from the directional speaker around the temple 14 of the frame of the eyeglass hearing aid.

In the example, a height of the temple 14 is 8 mm. Accordingly, the vertical difference between the two speakers/output transducers (SP1, SP2) (or the respective outlets of the two speakers) is 8 mm. The ear canal 3 (E.C.) is positioned 25 mm below the output transducer SP1.

Further, in the example, the speaker/output transducer SP2 is placed 17.2 mm closer to the microphones (mic) than the speaker/output transducer SP1.

Namely, if the sample rate of the digital signal processing unit is 20 kHz, then the 17.2 mm is equal to one sample delay:

$$x = c/fs = (344 \text{ m/s})/(20000 \text{ Hz}) = 0.0172 \text{ m}$$

For the present example, it is assumed that the two output transducers SP1, SP2 are point sources in a free field condition.

Under such assumption, the gain of the output transducer SP2 needs to be 2.1 dB lower than the gain of the output transducer SP1 to match the needed ratio between the outputs:

$$\begin{aligned}\text{Gain difference} &= 20 * \log10(\text{Distance 1}/\text{Distance 2}) \\ &= 20 * \log10(80[\text{mm}]/(80 - 17.2)[\text{mm}]) \\ &= 2.1 \text{ dB}\end{aligned}$$

Here, distance 1 corresponds to the distance between the output transducers SP1 and the microphone (mic).

Further, distance 2 corresponds to the distance between the output transducers SP2 and the microphone (mic).

As can be seen in FIG. 11, the output level (i.e., simulated sound pressure) at the ear canal 3 is 7.6 dB higher at 3 kHz than for the above-discussed dipole speaker, and the output level at the microphone is similar to that of the above-discussed dipole speaker, i.e., −40 dB.

While in this example, the speaker/output transducer SP2 is placed 17.2 mm closer to the microphones (mic) than the speaker/output transducer SP1, the position of the speaker outlet SP2 on the top of the temple of the glasses may be placed at a distance closer to the microphones that equals the distance that sound propagates at an integer multiple of the sample time of the signal processing unit. Namely, at a temperature of 20° C., at an exemplary sample frequency of 20 kHz, the sample time would be 50 μs, and sound would propagate 17.2 mm in 50 μs under these conditions. That is, under these conditions, the position of the speaker outlet SP2 on the top of the temple of the glasses may be placed at a distance closer to the microphones that equals an integer multiple of 17.2 mm.

The height of the temple and the vertical distance between the two speakers/output transducers (SP1, SP2) (or the respective outlets of the two speakers) is not limited to 8 mm.

In order to avoid mechanical feedback problems, according to the present disclosure, the two speakers OT1/SP1, OT2/SP2 of the directional speaker may be arranged so that the vibrations from each speaker is cancelled out.

Further, in order to minimize mechanical feedback, according to the present disclosure, each of the two speakers OT1/SP1, OT2/SP2 of the directional speaker may be a dual speaker.

Further, the number of speakers of the directional speaker is not limited to 2. Contrary thereto, the directional speaker of the present disclosure may be formed by more than two speakers, and with more than two speaker outlets.

When the directional speaker is combined with a bone conducting speaker placed in the temple 14 of the glasses (eyeglass hearing aid), since the bone conducting transceiver/speaker is good at transmitting low frequency sound signals <2 kHz, and the air conducting directional speaker is good at transmitting high frequency signals >1 kHz, the respective transceivers/speakers may be controlled with signals in the corresponding frequency bands only.

According to a further advantageous modification of the eyeglass hearing aid including a directional speaker, the directional speaker may be combined with directional microphone arrays. The directional microphone array may be used for both spatial filtering of the external sounds as well as a near field attenuation of the acoustical feedback from the speaker(s).

According to a further advantageous modification of the eyeglass hearing aid including a directional speaker, the frame of the eyeglass hearing aid may comprise sensors such as a light receiving element, i.e., photodetector. Such photodetector may be configured for visible light, or may be configured for infrared (IR) light, but is not limited thereto.

Namely, the eyeglass may be configured to emit IR light into the eye of the user and receive the backscattered light, where the backscattered light is converted into an electrical signal via the photodetector. The corresponding electrical signal may include information regarding the movement of the eyes. The movement of the eyes may be used to control the sound processing, e.g. the directivity of the microphones.

In particular, a light source may be provided on the frame of the eyeglass and may point towards the eye(s), wherein and the photodetector may be placed on the frame as well and may be configured to receive the backscattered light.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. An eyeglass hearing aid, comprising:
a carrier unit, the carrier unit forming a temple of said eyeglass hearing aid,
a frame of said eyeglass hearing aid, said frame including said temple,
at least one microphone unit provided on said frame of said eyeglass hearing aid,
a directional speaker unit configured to direct sound towards an ear canal of said user and to attenuate sound towards said at least one microphone unit,
a signal processing unit configured to output signals to said directional speaker unit, and
a vibrator unit provided on said carrier unit, wherein
said vibrator unit is configured to apply vibrations to a pinna of an outer ear of a user by touching said pinna,
said vibrator unit is mounted on said temple of said eyeglass hearing aid,
said directional speaker unit comprises a first speaker unit and a second speaker unit arranged such that a distance between said first speaker unit or a speaker outlet of said first speaker unit and said at least one microphone unit is substantially same as a distance between said second speaker unit or a speaker outlet of said second speaker unit and said at least one microphone unit, and
said first speaker unit and said second speaker unit are connected in series or parallel and opposite in phase.

2. The hearing aid according to claim 1, wherein
said vibrator unit is configured to touch a rear part of said pinna, and/or
said vibrator unit is configured to vibrate substantially perpendicular to a touching interface with said pinna.

3. The hearing aid according to claim 1, wherein
said hearing aid is a behind-the-ear hearing aid,
said carrier unit is a housing of said behind-the-ear hearing aid, and
said vibrator unit is mounted on said housing of said behind-the-ear hearing aid.

4. The hearing aid according to claim 3, further comprising
a speaker unit, a speaker driver unit configured to drive said speaker unit, and an earpiece, wherein said speaker unit is electrically connected to said speaker driver unit, and said speaker unit is provided in said earpiece or said speaker unit is provided in said housing of said behind-the-ear hearing aid and connected to said earpiece by means of a sound tube.

5. The hearing aid according to claim 3, further comprising at least one microphone unit, and a vibrator driver unit configured to drive said vibrator unit, wherein said vibrator driver unit is configured to, if said at least one microphone unit is activated, deactivate driving said vibrator unit.

6. An eyeglass hearing aid comprising:

a carrier unit the carrier unit forming a temple of said eyeglass hearing aid;

a vibrator unit provided on said carrier unit;

a frame of said eyeglass hearing aid, said frame including said temple;

at least one microphone unit provided on said frame of said eyeglass hearing aid;

a directional speaker unit configured to direct sound towards an ear canal of said user and to attenuate sound towards said at least one microphone unit; and a signal processing unit configured to output signals to said directional speaker unit, wherein said vibrator unit is configured to apply vibrations to a pinna of an outer ear of a user by touching said pinna, said vibrator unit is mounted on said temple of said eyeglass hearing aid, said directional speaker unit comprises a first speaker unit and a second speaker unit arranged such that a distance between said first speaker unit or a speaker outlet of said first speaker unit and said at least one microphone unit is larger than a distance between said second speaker unit or a speaker outlet of said second speaker unit and said at least one microphone unit, and said signal processing unit is configured to output a first signal to said first speaker unit and to output a second signal different from said first signal to said second speaker unit.

7. The hearing aid according to claim 6, wherein said signal processing unit is configured to apply said first signal with a delay and a gain with respect to said second signal.

8. The hearing aid according to claim 6, wherein said signal processing unit is configured to multiply said first signal with a weighting including at least one of an amplitude value and a phase value.

9. The hearing aid according to claim 8, wherein said weighting is frequency band dependent.

10. The hearing aid according to claim 6, wherein a difference between said distance between said first speaker unit or said speaker outlet of said first speaker unit and said at least one microphone unit and said distance between said second speaker unit or said speaker outlet of said second speaker unit and said at least one microphone unit is a difference distance, said signal processing unit is configured to process signals with a predetermined sample time, and said difference distance equals a distance that sound propagates at a numerical multitude of said predetermined sample time.

11. The hearing aid according to claim 1, wherein each of said first speaker unit and said second speaker unit is provided with a respective vibration cancellation unit configured to cancel out vibrations from said respective speaker unit towards said frame of said eyeglass hearing aid.

12. The hearing aid according to claim 1, wherein said vibrator unit is an electrodynamic transducer, a balanced electrodynamic separation transducer, or a piezo electrical transducer.

13. The hearing aid according to claim 2, wherein said hearing aid is a behind-the-ear hearing aid, said carrier unit is a housing of said behind-the-ear hearing aid, and said vibrator unit is mounted on said housing of said behind-the-ear hearing aid.

14. The hearing aid according to claim 4, further comprising at least one microphone unit, and a vibrator driver unit configured to drive said vibrator unit, wherein said vibrator driver unit is configured to, if said at least one microphone unit is activated, deactivate driving said vibrator unit.

15. The hearing aid according to claim 2, wherein said hearing aid is an eyeglass hearing aid, said carrier unit is a temple of said eyeglass hearing aid, and said vibrator unit is mounted on said temple of said eyeglass hearing aid.

16. The hearing aid according to claim 7, wherein a difference between said distance between said first speaker unit or said speaker outlet of said first speaker unit and said at least one microphone unit and said distance between said second speaker unit or said speaker outlet of said second speaker unit and said at least one microphone unit is a difference distance, said signal processing unit is configured to process signals with a predetermined sample time, and said difference distance equals a distance that sound propagates at a numerical multitude of said predetermined sample time.

17. The hearing aid according to claim 8, wherein a difference between said distance between said first speaker unit or said speaker outlet of said first speaker unit and said at least one microphone unit and said distance between said second speaker unit or said speaker outlet of said second speaker unit and said at least one microphone unit is a difference distance, said signal processing unit is configured to process signals with a predetermined sample time, and said difference distance equals a distance that sound propagates at a numerical multitude of said predetermined sample time.

* * * * *